(12) United States Patent
Tanaka et al.

(10) Patent No.: US 8,147,753 B2
(45) Date of Patent: Apr. 3, 2012

(54) HEAT EXCHANGER FOR MEDICAL USE AND ARTIFICIAL HEART-LUNG MACHINE

(75) Inventors: Minoru Tanaka, Hiroshima (JP);
Tomokazu Niitsuma, Hiroshima (JP);
Shigeki Kawarabata, Hiroshima (JP);
Takashi Matsushita, Hiroshima (JP)

(73) Assignee: JMS Co., Ltd., Hiroshima (JP)

( * ) Notice: Subject to any disclaimer, the term of this patent is extended or adjusted under 35 U.S.C. 154(b) by 430 days.

(21) Appl. No.: 12/593,707

(22) PCT Filed: Mar. 28, 2008

(86) PCT No.: PCT/JP2008/056180
§ 371 (c)(1),
(2), (4) Date: Sep. 29, 2009

(87) PCT Pub. No.: WO2008/120747
PCT Pub. Date: Oct. 9, 2008

(65) Prior Publication Data
US 2010/0114004 A1 May 6, 2010

(30) Foreign Application Priority Data

Mar. 30, 2007 (JP) .................. 2007-094772
Mar. 30, 2007 (JP) .................. 2007-094773

(51) Int. Cl.
*A61M 1/00* (2006.01)
*A61M 37/00* (2006.01)
(52) U.S. Cl. .............. 422/45; 422/44; 422/46; 422/47; 422/48

(58) Field of Classification Search .............. 96/8, 10; 604/4.01, 5.01, 6.01, 6.09, 6.13, 6.14; 422/44–48
See application file for complete search history.

(56) References Cited

U.S. PATENT DOCUMENTS

| 5,084,244 | A | 1/1992 | Muramoto |
| 5,876,667 | A | 3/1999 | Gremel et al. |
| 5,951,949 | A | * | 9/1999 | Olsen .............................. 422/46 |
| 2007/0166190 | A1* | 7/2007 | Ogihara et al. ................. 422/45 |

FOREIGN PATENT DOCUMENTS

EP 1 715 279 A1 10/2006
(Continued)

*Primary Examiner* — Leslie Deak
(74) *Attorney, Agent, or Firm* — Hamre, Schumann, Mueller & Larson, P.C.

(57) ABSTRACT

A heat exchanger includes a plurality of tubes 2 through an inner cavity of which a heat-transfer medium liquid flows, a sealing member 6 that seals the plurality of tubes 2 while exposing both ends thereof, with a blood channel passing outside each of the tubes 2 being formed in a central portion in the axial direction of the tubes, and a housing 5 that accommodates the tubes 2 sealed with the sealing member 6. The heat exchanger further includes a hollow fiber membrane 3 that is formed of a plurality of hydrophobic and gas permeable hollow fibers 4 and that is disposed on at least one of an entrance side and an exit side of the blood channel in the housing 5 so that a liquid flowing through the blood channel passes through the hollow fiber membrane 3. The housing 5 includes openings 10 for exposing open ends of each of the hollow fibers 4 forming the hollow fiber membrane 3 to the outside, and gaps between an inner side of the openings and the hollow fibers 4 are sealed. Air can be removed while suppressing a reduction in the heat exchange efficiency.

8 Claims, 14 Drawing Sheets

FOREIGN PATENT DOCUMENTS

| | | |
|---|---|---|
| JP | 2-109572 A | 4/1990 |
| JP | 6-014965 B | 3/1994 |
| JP | 8-024333 A | 1/1996 |
| JP | 11-047269 A | 2/1999 |
| JP | 11-509451 A | 8/1999 |
| JP | 2000-515055 A | 11/2000 |
| JP | 2005-224301 A | 8/2005 |
| JP | 2006-212075 A | 8/2006 |

* cited by examiner

HEAT EXCHANGER FOR MEDICAL USE AND ARTIFICIAL HEART-LUNG MACHINE

TECHNICAL FIELD

The present invention relates to a heat exchanger, in particular, a heat exchanger for medical use that is suitable for use in a medical device such as an artificial heart-lung machine, and to an artificial heart-lung machine equipped with the heat exchanger.

BACKGROUND ART

In heart surgery and the like, an artificial heart-lung machine is used to take over the respiratory function and the circulatory function of a patient under going the surgery. Moreover, during the surgery, in order to reduce the oxygen consumption by the patient, it is necessary to lower the patient's body temperature and maintain the lowered body temperature. For this purpose, the artificial heart-lung machine is equipped with a heat-exchanging portion and thereby controls the temperature of blood taken from the patient.

Now, the configuration of a conventional example of an artificial heart-lung machine will be described using FIG. 14. FIG. 14 is a cross-sectional view schematically showing the configuration of a conventional example of an artificial heart-lung machine. This artificial heart-lung machine includes a heat-exchanging portion (heat exchanger) 130 that performs blood temperature control and a gas-exchanging portion (artificial lung) 131.

The heat-exchanging portion 130 and the gas-exchanging portion 131 are accommodated in a housing 122. A cold/warm water supply port 123 for introducing cold/warm water for heat exchange and a cold/warm water discharge port 124 for discharging the cold/warm water are provided in a segment of the housing 122 corresponding to the heat-exchanging portion 130. A gas supply port 125 for introducing oxygen gas and a gas discharge port 126 for discharging carbon dioxide and the like in blood are provided in a segment of the housing 122 corresponding to the gas-exchanging portion 131.

The heat-exchanging portion 130 includes a plurality of metal tubes 101 arranged parallel to one another within a housing 102. Each tube 101 communicates with the cold/warm water supply port 123 and the cold/warm water discharge port 124, and cold/warm water flows through the interior of the tube 101. Moreover, an inlet port 106 for introducing blood removed from a patient is provided in an upper face of the housing 102. Blood that has undergone heat exchange in the heat-exchanging portion 130 flows toward the gas-exchanging portion 131.

Moreover, a sealing member 103 (shown with dots by hatching in the areas where the sealing member 103 is formed) is provided within the heat-exchanging portion 130. The sealing member 103 seals the blood flowing within the heat-exchanging portion 130 while coming into contact with the surface of the tubes 101, thereby forming a blood channel 108 for the blood introduced from the inlet port 106. The sealing member 103 is formed by filling spaces between the tubes with a resin material in such a manner that opposite both open ends of the plurality of tubes 101 are not blocked.

The gas-exchanging portion 131 is formed by laminating a plurality of hollow fiber sheets 105. The hollow fiber sheets 105 are formed by bundling a plurality of hollow fibers with lateral yarns. A sealing member 104 (shown with dots by hatching in the areas where the sealing member 104 is formed) is also provided within the gas-exchanging portion 131. The sealing member 104 seals the blood flowing within the gas-exchanging portion 131 while coming into contact with the surface of the hollow fibers constituting the hollow fiber sheets 105, and thereby forms a blood channel 113 within the gas-exchanging portion 131.

The sealing member 104 is formed by filling spaces between the hollow fibers with a resin material in such a manner that opposite open ends of the hollow fibers constituting the hollow fiber sheets 105 are not blocked. The gas supply port 125 and the gas discharge port 126 are in communication with each other through the hollow fibers constituting the hollow fiber sheets 105.

With the above-described configuration, blood passing through the blood channel 108 in the heat-exchanging portion 130 while exchanging heat flows into the blood channel 113 in the gas-exchanging portion 131, so as to come into contact with the hollow fibers. At this time, oxygen gas flowing through the hollow fibers is taken in by the blood. The blood that has taken in the oxygen gas is discharged to the outside from a blood outlet port 107 provided in the housing 122, and returned into the patient. On the other hand, carbon dioxide in the blood is taken in by the hollow fiber sheets 105 and then discharged from the gas discharge port 126 to the outside of the artificial heart-lung machine.

Moreover, in the case where an artificial heart-lung machine is used, in order to remove air and foreign matter from a blood circuit and allow the hollow fibers of the gas-exchanging portion 131 to acclimatize to liquid, priming is performed beforehand using a priming liquid such as a physiological saline solution, and blood circulation is performed thereafter. However, even when priming has been performed, air may mix into the blood during the blood circulation, and so it is required to equip the artificial heart-lung machine with a function for removing air. With such a function, priming can be finished in a short period of time, which is effective in medical emergencies. Thus, various artificial heart-lung machines equipped with a function for removing air have been proposed conventionally (see Patent Documents 1 to 3).

For example, an artificial heart-lung machine disclosed in Patent Document 1 uses hollow fibers as the tubes of a heat-exchanging portion. A side wall of the hollow fibers is formed of a porous membrane and a thin film of silicone rubber covering the exterior of the porous membrane, and is permeable only to gas. Moreover, in this artificial heart-lung machine, the pressure of cold/warm water flowing inside the hollow fibers is set to be lower than the pressure of blood flowing outside the hollow fibers. This allows air in the blood to be taken into the interior of the hollow fibers through the side wall of the hollow fibers and separated from the blood.

According to the artificial heart-lung machines disclosed in Patent Documents 2 and 3, a heat-exchanging portion has a plurality of metal tubes, but unlike the example in FIG. 14, blood flows through the interior of the tubes and cold/warm water flows over the surface of the tubes. Moreover, the heat-exchanging portion includes, on an entrance side of the tubes, a space for temporarily storing blood and an inlet port that causes the blood to flow into the space while swirling.

In the heat-exchanging portion of the artificial heart-lung machines of Patent Document 2 and 3, blood and air are separated from each other by a centrifugal force caused by the swirling of the blood, and only the blood from which air has been removed is transferred into the tubes of the heat-exchanging portion. Furthermore, in Patent Document 3, the heat-exchanging portion includes another space for temporarily storing blood on an exit side of the tubes, and a valve through which this space can communicate with the outside is provided in a wall face of this space. With the heat-exchanging portion of Patent Document 3, air is removed more reliably.

Patent Document 1: JP 8-24333 A
Patent Document 3: JP 11-47269 A
Patent Document 2: JP 6-14965 B

DISCLOSURE OF INVENTION

Problem to be Solved by the Invention

In the artificial heart-lung machine disclosed in Patent Document 1, it is necessary for the tubes constituting the heat-exchanging portion to perform both heat exchange and the removal of air. Accordingly, it is difficult simultaneously to improve both of the air-removal performance and the heat-exchange performance, and when emphasis is placed on the air-removal performance, the heat-exchange performance decreases. Conversely, when emphasis is placed on the heat-exchange performance, the air-removal performance decreases.

Moreover, in the artificial heart-lung machines of Patent Documents 2 and 3, it is necessary for the blood to flow through the interior of thin tubes. Accordingly, thrombi tend to be generated in the interior of the tubes, and there is a problem in that this also reduces the heat exchange efficiency of the heat-exchanging portion. Moreover, the artificial heart-lung machines of Patent Documents 2 and 3 have complicated structures, so there also is a problem of high manufacturing costs.

It is an object of the present invention to address the above-described problems and provide a heat exchanger for medical use and an artificial heart-lung machine that are capable of removing air while suppressing the reduction in the heat exchange efficiency.

Means for Solving Problem

A heat exchanger for medical use of the present invention includes a plurality of tubes through an inner cavity of which a heat-transfer medium liquid flows, a sealing member that seals the plurality of tubes while exposing both ends thereof, with a blood channel passing outside each of the tubes being formed in a central portion in the axial direction of the tubes, and a housing that accommodates the tubes sealed with the sealing member.

In order to address the above-described problems, the heat exchanger further includes a hollow fiber membrane that is formed of a plurality of hydrophobic and gas permeable hollow fibers and that is disposed on at least one of an entrance side and an exit side of the blood channel in the housing so that a liquid flowing through the blood channel passes through the hollow fiber membrane. The housing includes openings for exposing open ends of each of the hollow fibers forming the hollow fiber membrane to the outside, and gaps between an inner side of the openings and the hollow fibers are sealed.

An artificial heart-lung machine of the present invention includes a heat-exchanging portion having a first blood channel and a gas-exchanging portion having a second blood channel. The heat-exchanging portion is arranged so that heat exchange is performed on blood flowing through the first blood channel, and the gas-exchanging portion is arranged so that gas exchange is performed on blood flowing through the second blood channel. The first blood channel and the second blood channel are in communication with each other, allowing a liquid to flow through the two blood channels. The heat-exchanging portion includes a plurality of tubes through an inner cavity of which a heat-transfer medium liquid flows, a first sealing member that seals the plurality of tubes while exposing both ends thereof, with a blood channel passing outside each of the tubes being formed in a central portion in the axial direction of the tubes, and a housing that accommodates the tubes sealed with the first sealing member. The gas-exchanging portion includes a first hollow fiber membrane formed of a plurality of hydrophobic and gas permeable hollow fibers, and a second sealing member that seals the first hollow fiber membrane while exposing both ends of the hollow fibers, with the second blood channel being formed so as to traverse the plurality of hollow fibers while coming into contact with an outer surface thereof.

In order to address the above-described problems, the heat-exchanging portion further includes a second hollow fiber membrane that is formed of a plurality of hydrophobic and gas permeable hollow fibers and that is disposed on at least one of an entrance side and an exit side of the first blood channel in the housing so that a liquid flowing through the first blood channel passes through the second hollow fiber membrane. The housing includes openings for exposing open ends of each of the hollow fibers forming the second hollow fiber membrane to the outside, and gaps between an inner side of the openings and the hollow fibers are sealed.

Effects of the Invention

The heat exchanger for medical use having the above-described configuration can release air within the heat exchanger and air mixed in a fluid (e.g., blood) to be subjected to heat exchange to the outside by means of the hollow fiber membrane provided on at least one of the entrance side and the exit side of the blood channel. As a result, sufficient air-removal performance can be obtained while maintaining sufficient heat-exchange performance, and there is no need to swirl the fluid to be subjected to heat exchange.

Figure 1:
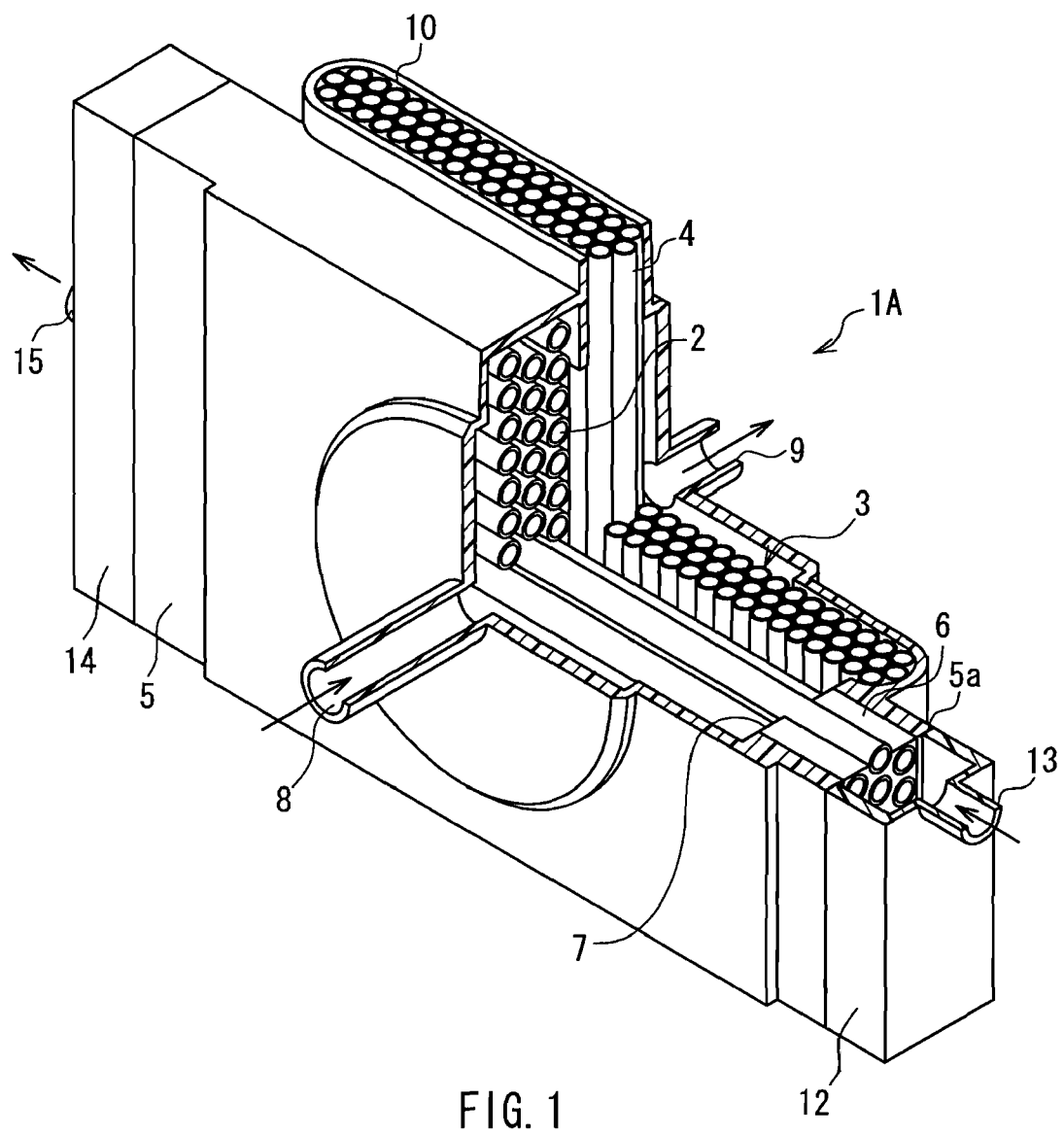
FIG. 1 is a perspective view schematically showing a configuration of a heat exchanger for medical use according to Embodiment 1 of the present invention.

DESCRIPTION OF REFERENCE NUMERALS 1A, 1B, 1C Heat exchanger
2 Tube
3 Hollow fiber membrane
4 Hollow fiber
5 Housing
5a, 5b Opening
6 Sealing member
7 First blood channel
8 Inlet port
9 Outlet port
10, 11 Opening for hollow fibers
12 Cover
13 Cold/warm water supply port
14 Cover
15 Cold/warm water discharge port
16 Cap member
17 Main member
17a Through hole
17b Inner space
18 Sheet member
19 Tube
20 Gas-exchanging portion
21 Hollow fiber layer
22 Hollow fiber
23 Channel for blood flow
24 Sealing member
25 Housing
26 Inlet port
27 Outlet port
28 Cover
29 Gas supply port
30 Cover
31 Gas discharge port
32, 33 Housing
34, 39 Cap member
35, 36 Cap
35a, 36a Space
35b, 36b Through hole
37 Bridge member
38 Sheet member
40 Tube
40a Coupling tube
40b Ventilating tube

DESCRIPTION OF THE INVENTION

The present invention has the above-described configurations as basic configurations, and the following embodiments are possible.

That is to say, it is preferable that the heat exchanger for medical use or the heat-exchanging portion of the artificial heart-lung machine having an above-described configuration further includes cap members that are attached to the openings of the housing and that seal the openings. This allows the interior of the hollow fibers constituting the hollow fiber membrane no longer to be in an open state when the openings are sealed with the cap members after priming is finished; thus, the occurrence of blood plasma leakage in the hollow fiber membrane is suppressed. This embodiment is effective in a situation where the removal of air is finished and the occurrence of blood plasma leakage is more problematic than air contamination.

Moreover, in the heat exchanger for medical use or the artificial heart-lung machine having the above-described configuration, a hollow fiber membrane formed by stacking a plurality of hollow fiber sheets formed by bundling a plurality of hollow fibers into a sheet form can be used as the hollow fiber membrane. Moreover, in this case, it is advantageous that the hollow fibers are made of a porous polypropylene, and the hollow fiber membrane is formed by stacking three to five hollow fiber sheets.

Hereinafter, a heat exchanger for medical use and an artificial heart-lung machine according to embodiments of the present invention will be described with reference to the drawings.

Embodiment 1

Figure 2:
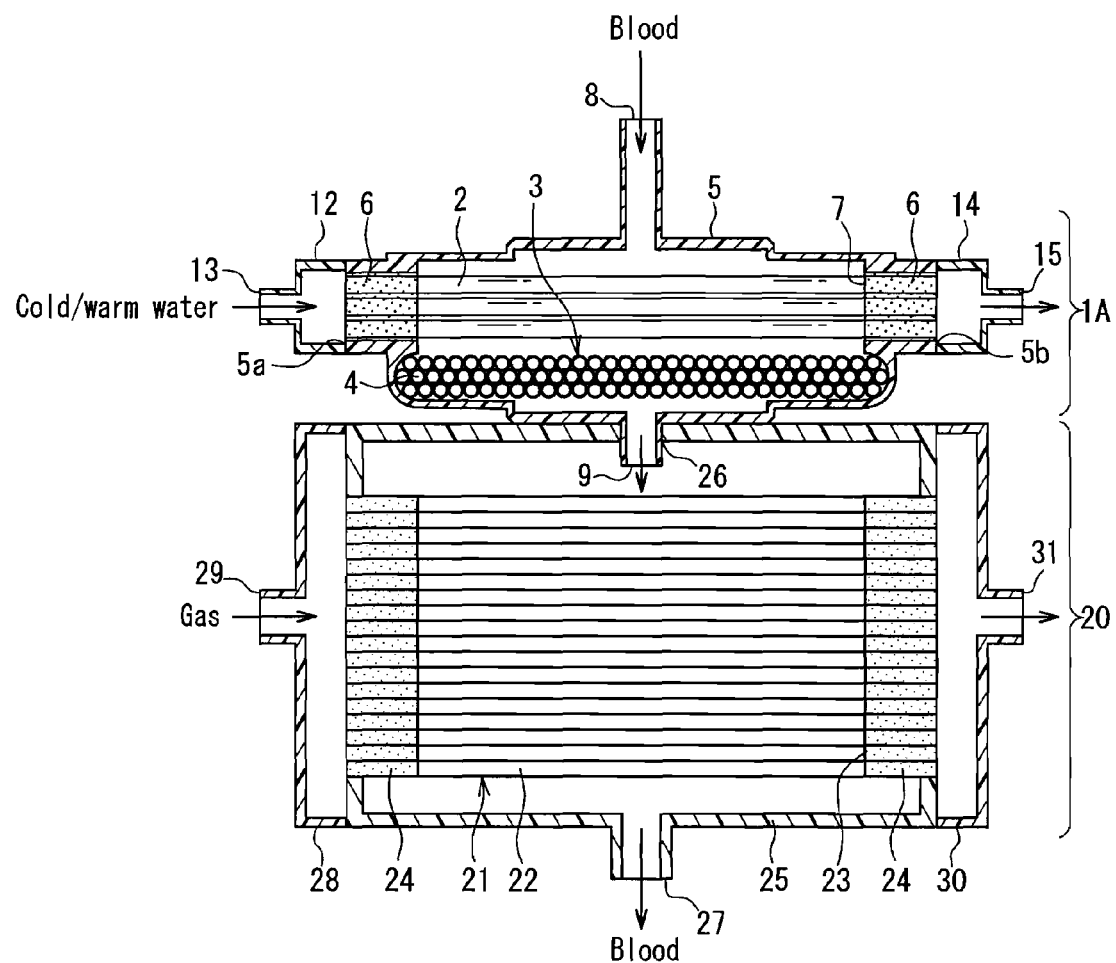
FIG. 2 is a cross-sectional view schematically showing a configuration of an artificial heart-lung machine including the same heat exchanger.

The configurations of a heat exchanger for medical use and an artificial heart-lung machine according to Embodiment 1 of the present invention will be described using FIGS. 1 and 2. FIG. 1 is a perspective view schematically showing the configuration of a heat exchanger 1A of the present embodiment. FIG. 2 is cross-sectional view schematically showing the configuration of an artificial heart-lung machine including the heat exchanger 1A of the present embodiment.

In FIG. 1, the heat exchanger 1A is shown partially sectioned. The heat exchanger 1A shown in FIG. 1 is used to control the temperature of blood removed from a patient and functions as a heat-exchanging portion of the artificial heart-lung machine shown in FIG. 2.

Figure 14:
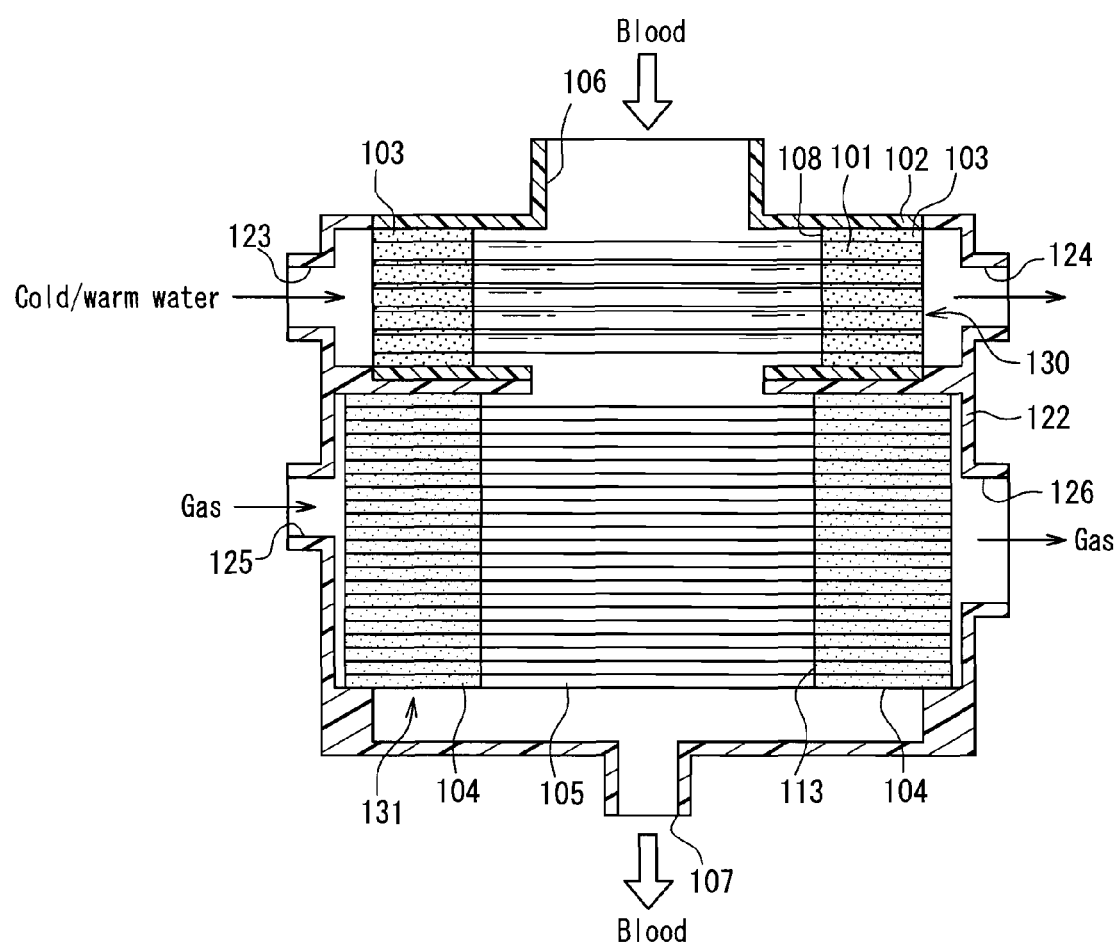
FIG. 14 is a cross-sectional view schematically showing the configuration of a conventional example of an artificial heart-lung machine.

As shown in FIGS. 1 and 2, the heat exchanger 1A includes a plurality of tubes 2, a housing 5 that accommodates the tubes 2, and a sealing member 6, similarly to the conventional heat exchanger for medical use shown in FIG. 14. The plurality of tubes 2 is made of a metal such as stainless steel, and cold/warm water for temperature control is passed through the interior thereof. The sealing member 6 seals the plurality of tubes 2 while exposing both ends of the tubes in such a manner that a first blood channel 7 passing outside each of the tubes 2 is formed in a central portion in the axial direction of the tubes 2 within the housing 5. Blood, a priming liquid, and the like are isolated from the cold/warm water flowing through the inner cavity of the tubes 2 by the sealing member 6 and flows through the first blood channel 7 while coming into contact with the outer surface of the plurality of tubes 2.

Although blood primarily is passed through the first blood channel 7 of the heat exchanger 1A, in some cases, other liquids such as a priming liquid or a medicine are passed therethrough. Moreover, in the present embodiment, the housing 5 includes, at positions corresponding to the first blood channel 7, an inlet port 8 for introducing blood into the housing 5 and a outlet port 9 for discharging the blood after heat exchange. Furthermore, the housing 5 includes two openings 5a and 5b at positions facing the open ends of the tubes 2. The sealing member 6 is formed in the vicinity of the openings 5a and 5b by filling gaps between end portions of the tubes 2 with a resin material.

The opening 5a to which one of the open ends of the tubes 2 is exposed is covered with a cover 12 in which a cold/warm water supply port 13 for introducing cold/warm water is provided. The other opening 5b (see FIG. 2) to which the other open end of the tubes 2 is exposed is covered with a cover 14 in which a cold/warm water discharge port 15 for discharging cold/warm water is provided.

Moreover, as shown in FIG. 2, the artificial heart-lung machine of the present embodiment includes a gas-exchanging portion 20 in addition to the heat-exchanging portion configured from the heat exchanger 1A shown in FIG. 1. The blood flowing out of the first blood channel 7 is discharged from the outlet port 9 and thereafter flows into the gas-exchanging portion 20 (see FIG. 2). The gas-exchanging portion 20 has the same configuration as the gas-exchanging portion of the conventional example of the artificial heart-lung machine shown in FIG. 14 and includes a hollow fiber layer 21. The hollow fiber layer 21 is configured by stacking a plurality of hollow fiber sheets formed by bundling a plurality of hollow fibers 22, and is accommodated within a housing 25.

Moreover, a sealing member 24 also is provided within the housing 25 of the gas-exchanging portion 20. The sealing member 24 is formed by filling spaces between the hollow fibers 22 with a resin material in such a manner that opposite open ends of each of the hollow fibers 22 are not blocked. A second blood channel 23 also is formed within the gas-exchanging portion 20 by the sealing member 24. This second blood channel is in communication with the first blood channel 7 of the heat exchanger 1A.

Furthermore, a pair of openings is formed at portions of the housing 25 that face the opposite open ends of each of the hollow fibers 22. Moreover, one of the pair of openings is covered with a cover 28 in which a gas supply port 29 is provided, and the other opening is covered with a cover 30 in which a gas discharge port 31 is provided.

As shown in FIGS. 1 and 2, the heat exchanger 1A and the artificial heart-lung machine of the present embodiment have the same basic configurations as the conventional example, as described above. However, in the present embodiment, the heat exchanger 1A is different from the heat exchanger of the conventional example in that a hollow fiber membrane 3 formed of a plurality of hollow fibers 4 having hydrophobicity and gas permeability is provided on an exit side of the first blood channel 7 in the housing 5. The blood flowing out of the first blood channel 7 passes through the hollow fiber membrane 3 on the exit side of the first blood channel 7 before flowing into the gas-exchanging portion 20.

Furthermore, in the heat exchanger 1A, the housing 5 includes an opening 10 for exposing an open end of each of the hollow fibers 4 forming the hollow fiber membrane 3 to the outside. In order also to expose an open end of the hollow fibers 4 that is not shown to the outside, an opening 10 also is provided on the opposite side of the shown portion. Moreover, gaps created between an outer face of both end portions of each of the hollow fibers 4 and an inner face of the openings 10 are filled with a resin material; thus, a leakage of blood from the openings 10 is prevented.

With the above-described configuration, according to the present embodiment, when a fluid such as blood is introduced from the inlet port 8, air that is present in the housing 5 of the heat exchanger 1A and air (air bubbles) mixed in the introduced fluid are transferred to the hollow fiber membrane 3 and released to the outside. For example, during priming, which is performed by introducing a priming liquid such as a physiological saline solution, air pushed out by the priming liquid is released to the outside of the heat exchanger 1A by the hollow fiber membrane 3. As a result, the priming operation can be simplified and expedited.

Accordingly, in the present embodiment, there is no need to add an air-removal function to the tubes 2 for heat exchange, and there is no need to use hollow fibers as the tubes 2. Metal pipes having high heat conductivity can be utilized as the tubes 2. Furthermore, in the present embodiment, there also is no need to swirl the blood to be subjected to heat exchange. Therefore, according to the present embodiment, a reduction in the heat exchange efficiency can be suppressed.

The hollow fiber membrane 3 is formed by bundling a plurality of hollow fibers 4 to form a hollow fiber sheet and stacking a plurality of hollow fiber sheets. The number of hollow fiber sheets to be stacked can be set appropriately with consideration given to the inflow resistance and the air-removal capacity. For example, in order to suppress an increase in the amount of priming of the heat exchanger 1A, it is advantageous to set the number of hollow fiber sheets to be stacked to about 3 to 5.

The hollow fiber membrane 3 has the same laminated structure as the hollow fiber layer 21 configuring the gas-exchanging portion 20 in that the hollow fiber membrane 3 is formed by stacking hollow fiber sheets. In the present embodiment, the hollow fiber layer 21 includes 1 to 20, preferably 3 to 5 layers of hollow fiber sheets.

Any gas permeable and hydrophobic hollow fiber, i.e., any hollow fiber having a side wall that allows only gas to pass through it but prohibits liquid to pass through it can be used as the hollow fibers 4 constituting the hollow fiber membrane 3. For example, the same hollow fibers as the hollow fibers 22 constituting the gas-exchanging portion 20 may be used as the hollow fibers 4 constituting the hollow fiber membrane 3. Specifically, an example of the hollow fibers 4 is hollow fibers made of a porous polypropylene or a porous polymethylpentene.

Out of the above-described two different types of hollow fibers, hollow fibers made of a porous polypropylene are preferable in terms of air-removal capacity. On the other hand, in the case where prolonged contact with blood is expected, hollow fibers made of a porous polymethylpentene are preferable. When polymethylpentene is used, a layer with densely packed pores, which is known as a "skin layer", can be formed on the surface of the hollow fibers 4, whereby the occurrence of blood plasma leakage that is caused by prolonged contact with blood can be suppressed.

It should be noted that when blood is introduced into the heat exchanger 1A after the priming operation is finished, blood may cause the loss of hydrophobicity of the hollow fibers 4 and, consequently, blood plasma leakage may occur. Therefore, in the present embodiment, it is preferable to take measures to address blood plasma leakage.

Blood plasma leakage refers to a phenomenon in which the proteins in the blood cause the surface of a hollow fiber to lose its hydrophobicity and, thereafter, blood seeps into the interior of the hollow fibers 4, resulting in blood leakage. In the present embodiment, in view of the necessity for the removal of air, the pressure in the interior of the hollow fibers 4 constituting the hollow fiber membrane 3 of the heat exchanger 1A is set to be lower than the pressure of the influent blood (atmospheric pressure). Therefore, blood plasma leakage is more likely to occur in the hollow fibers 4 than in the hollow fibers 22 constituting the hollow fiber layer 21 of the gas-exchanging portion 20. It should be noted that in the case of introducing a liquid containing no protein like a priming liquid, the hydrophobicity of the surface of the hollow fibers is not lost, and problems like blood plasma leakage do not arise.

Thus, it is preferable that the heat exchanger 1A is provided with cap members 16 shown in FIGS. 3 to 5 below. The cap members 16 are effective particularly in the case where the hollow fiber membrane 3 of the heat exchanger 1A is formed from hollow fibers made of a porous polypropylene and blood plasma leakage is likely to occur. The suppression of blood plasma leakage by the cap members 16 will be described using FIGS. 3 to 5.

Figure 3:
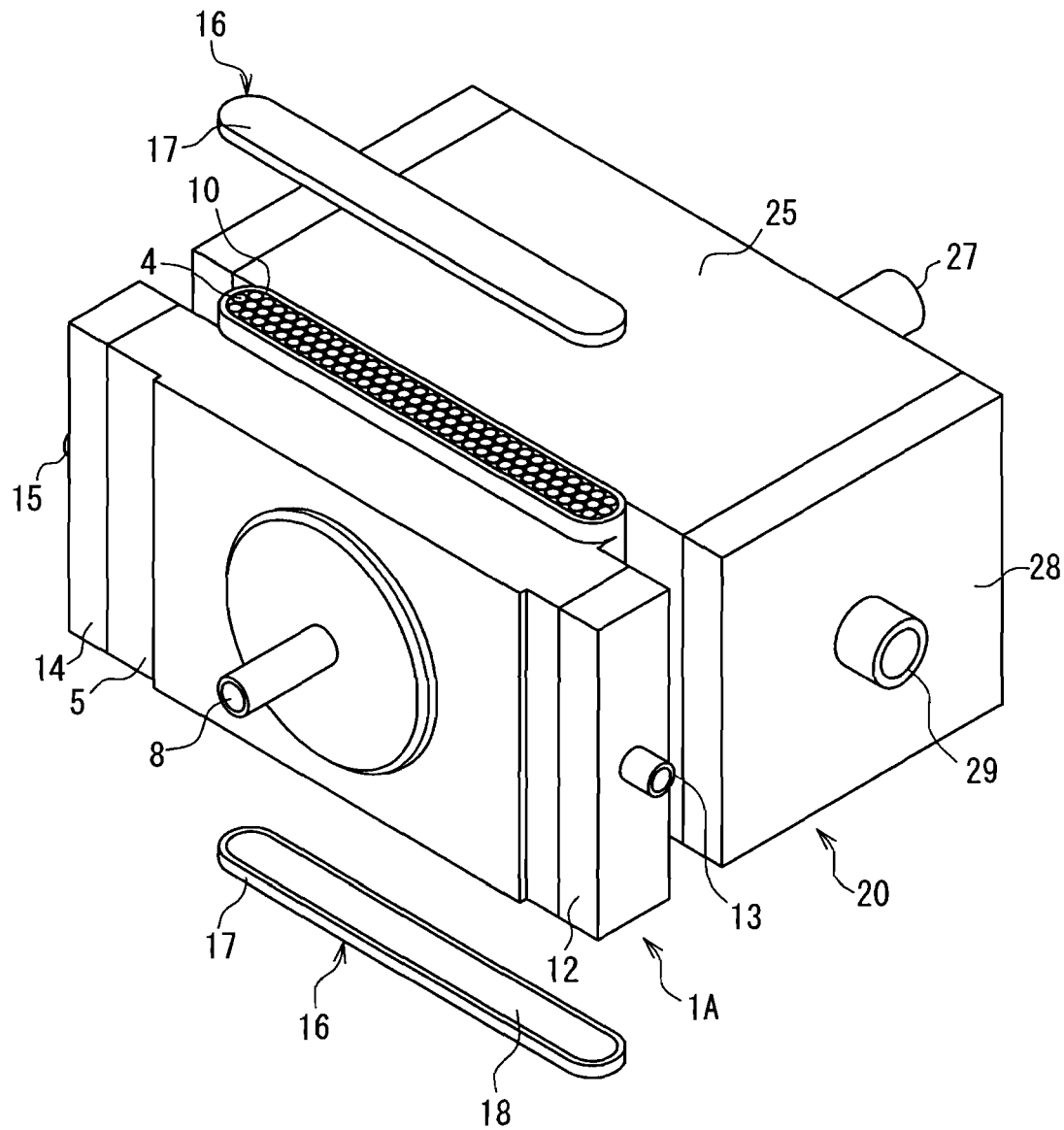
FIG. 3 is a perspective view showing an external appearance of the artificial heart-lung machine in which the same heat exchanger is provided with cap members.

FIG. 3 is a perspective view showing an external appearance of the artificial heart-lung machine provided with the cap members 16. FIG. 4 is a cutaway perspective view showing the heat exchanger with the cap members 16 shown in FIG. 3 attached thereto. FIG. 5 is a cutaway perspective view showing the heat exchanger with another form of the cap members 16 attached thereto.

Figure 4:
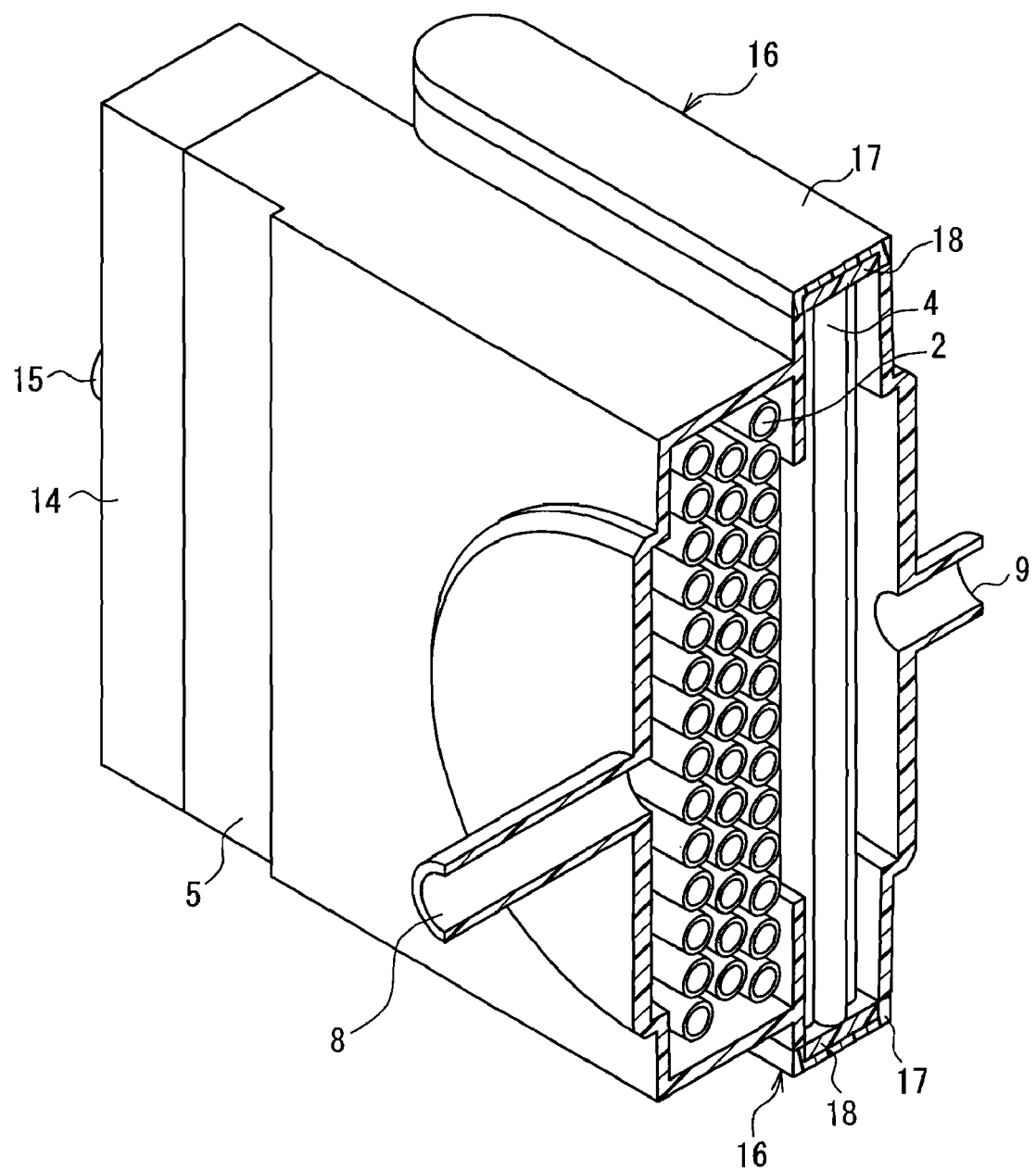
FIG. 4 is a cutaway perspective view showing the same heat exchanger with the cap members attached thereto.

As shown in FIGS. 3 and 4, the cap members 16 are attached to the openings 10 provided in the housing 5 of the heat exchanger 1A so as to cover the openings 10. In the present embodiment, the cap members 16 are attached after priming is finished.

The cap members 16 each include a lid-like main member 17 that is formed so as to conform to the shape of the opening 10, and a sheet member 18 that is disposed on the inside of the main member 17. The sheet member 18 is made of an elastic material such as silicone rubber. Therefore, after the attachment of the cap members 16 to the openings, the open ends of the hollow fibers 4 constituting the hollow fiber membrane 3 are hermetically closed by the sheet members 18, and the openings 10 are in a sealed state.

Thus, after the attachment of the cap members 16, the hollow fibers 4 are no longer in an open state, and it is difficult for a fluid to enter and exit the hollow fibers 4. Consequently, even in the case where the hydrophobicity of the hollow fibers 4 is lost due to prolonged contact with blood, blood cannot intrude into the interior of the hollow fibers 4 through the side wall thereof; thus, blood plasma leakage is suppressed.

Figure 5:
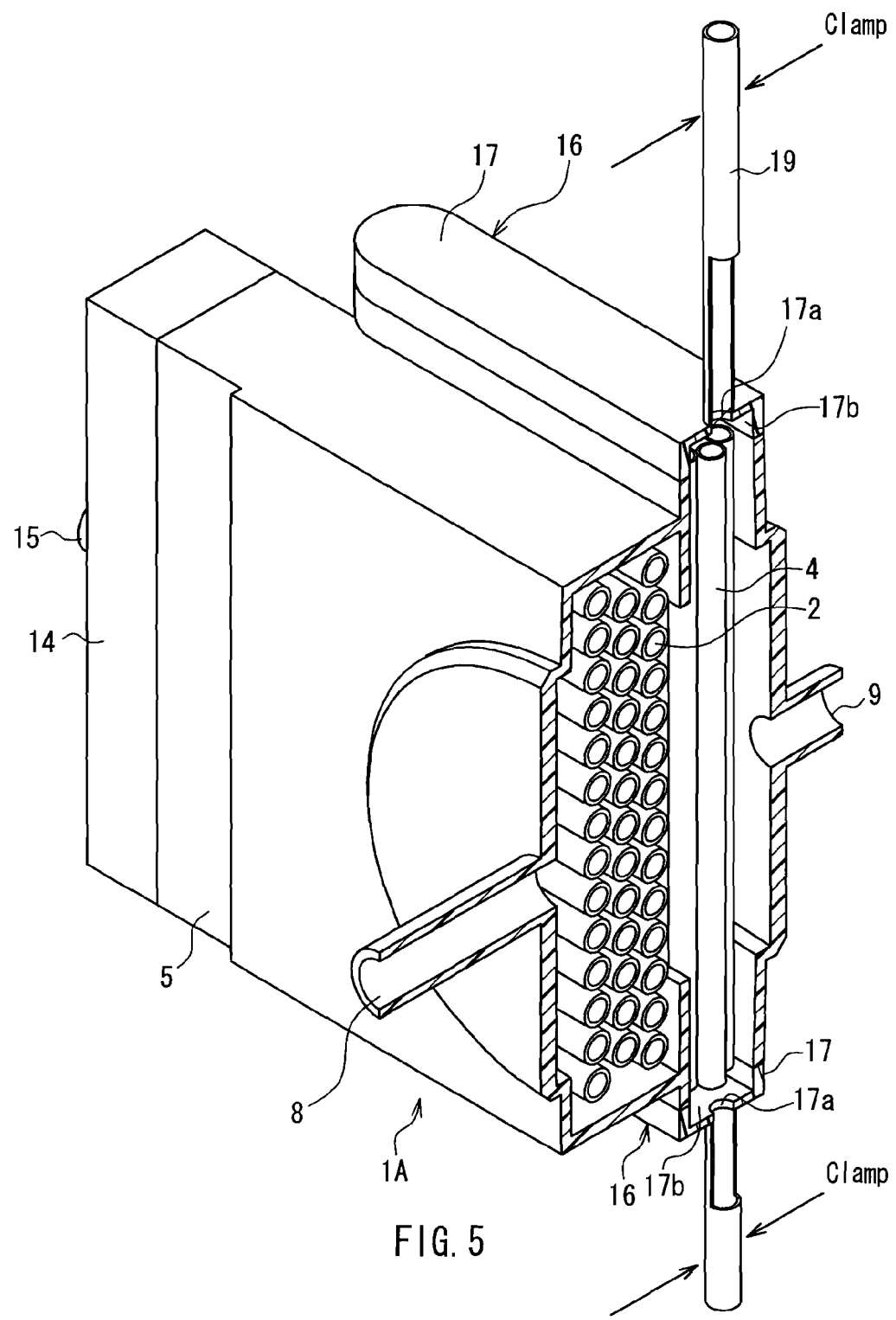
FIG. 5 is a cutaway perspective view showing the heat exchanger with cap members of another form attached thereto.

The cap members 16 also may be in a form as shown in FIG. 5. In the example shown in FIG. 5, the cap members each include a tube 19 instead of the sheet member 18 (see FIG. 4). The tube 19 is in communication with a space 17b on the inside of the main boy 17 via a through hole 17a provided in the main member 17.

When the cap members 16 shown in FIG. 5 are merely disposed, the openings 10 are not in a sealed state, and the hollow fibers 4 are open to the air through the tubes 19 as in the case where the cap members 16 are not disposed. However, as shown in FIG. 5, when the tubes 19 are obstructed by clamping the tubes 19, the openings 10 are in a sealed state, and the hollow fibers 4 are no longer in an open state. Also in this case, it is difficult for a fluid to enter and exit the hollow fibers 4; thus, blood plasma leakage is suppressed. The use of the cap members 16 shown in FIG. 5 enables a user to seal and unseal the openings 10 with a simple operation.

Embodiment 2

Figure 6:
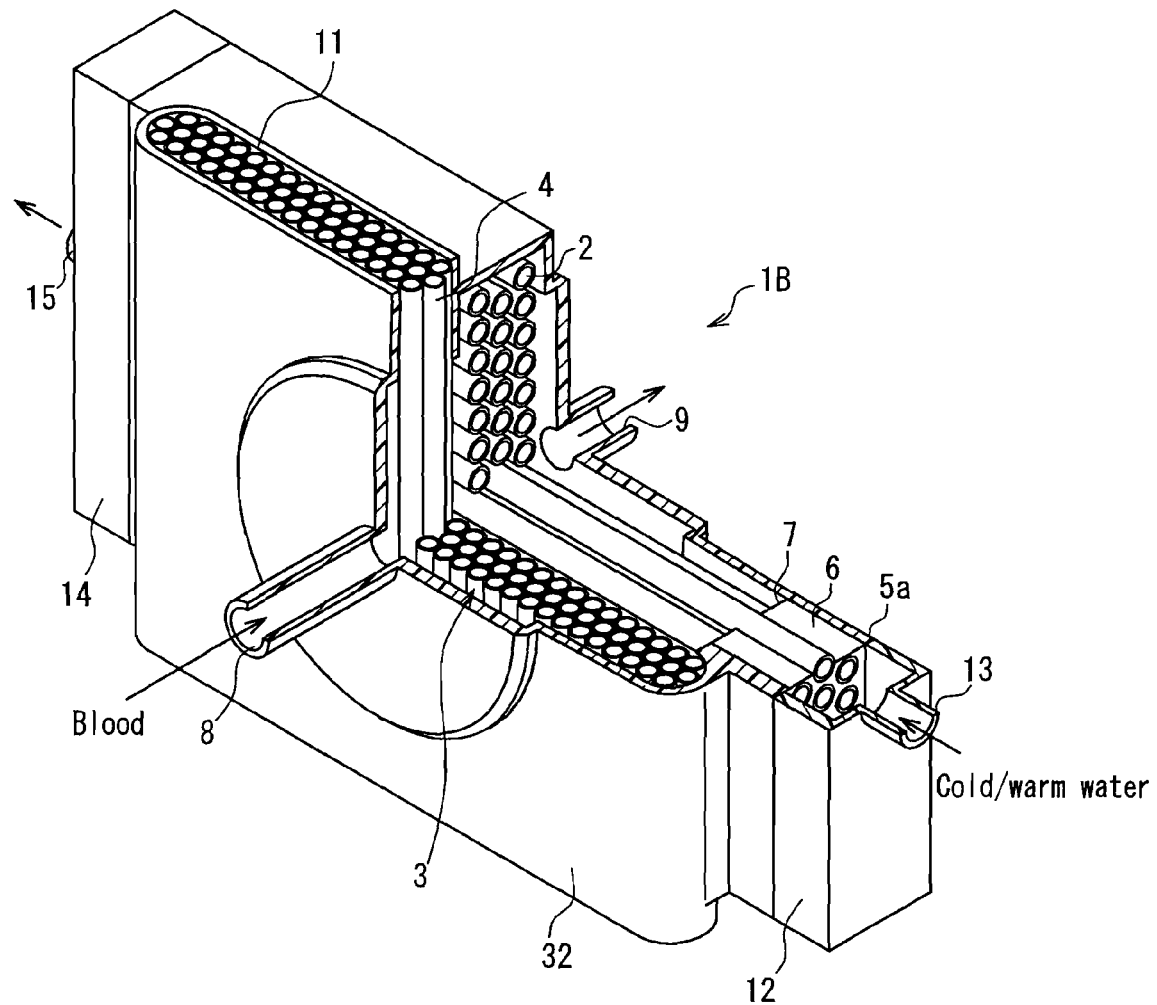
FIG. 6 is a perspective view schematically showing a configuration of a heat exchanger for medical use according to Embodiment 2 of the present invention.
Figure 7:
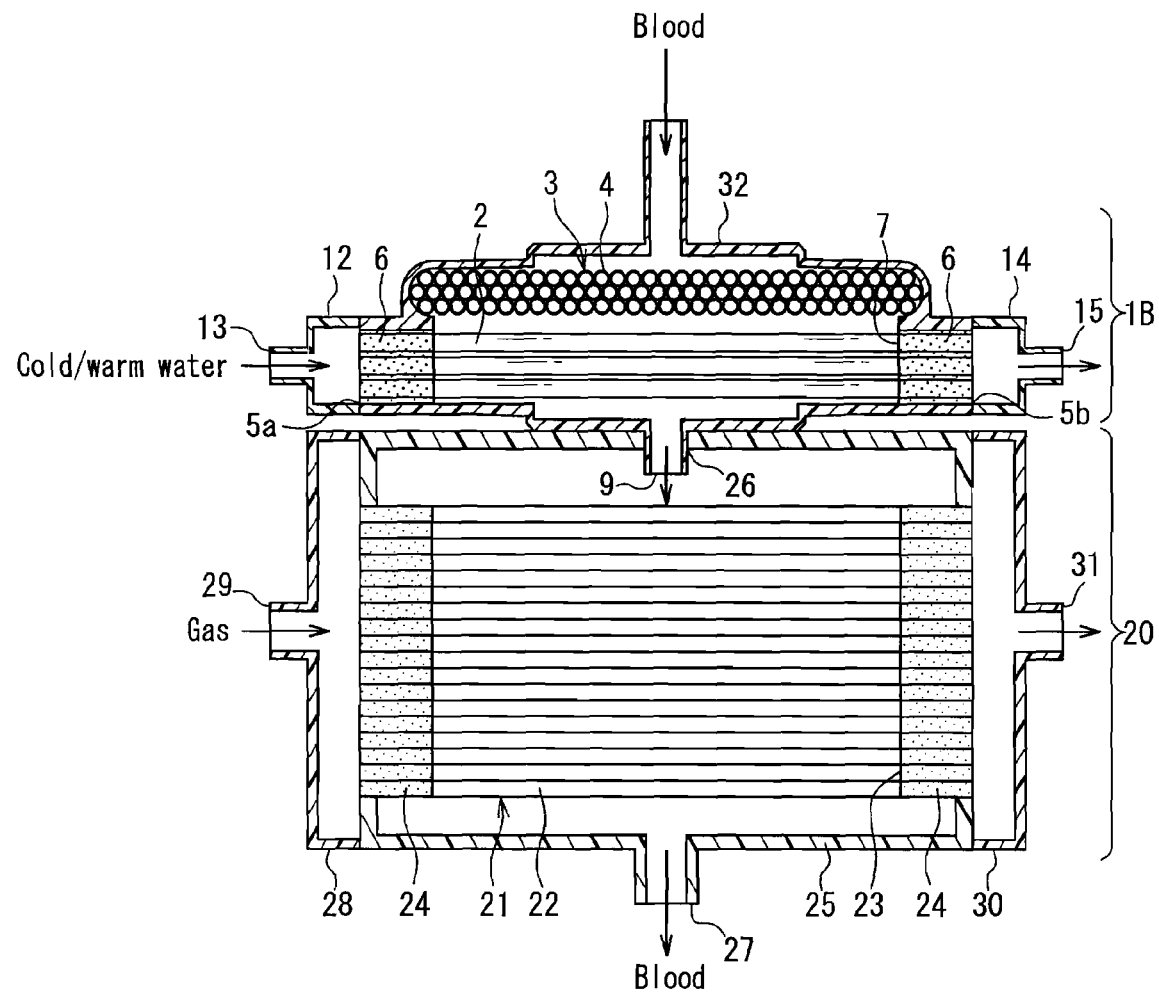
FIG. 7 is a cross-sectional view schematically showing a configuration of an artificial heart-lung machine including the same heat exchanger.

The configurations of a heat exchanger and an artificial heart-lung machine according to Embodiment 2 of the present invention will be described using FIGS. 6 and 7. FIG. 6 is a perspective view schematically showing the configuration of a heat exchanger 1B of the present embodiment. FIG. 7 is a cross-sectional view schematically showing the configuration of an artificial heart-lung machine including the heat exchanger 1B of the present invention. In FIGS. 6 and 7, the same elements as those of the heat exchanger and the artificial heart-lung machine of Embodiment 1 shown in FIGS. 1 and 2 are given the same reference numerals, and a repeated description thereof will be omitted for the sake of simplicity In the heat exchanger 1B of the present embodiment, a hollow fiber membrane 3 is disposed on an entrance side of a first blood channel 7 in a housing 32. The housing 32 includes openings 11 for exposing open ends of each of hollow fibers 4 forming the hollow fiber membrane 3 to the outside. The configuration of the hollow fiber membrane 3 and the configuration of the housing 32 for accommodating the hollow fiber membrane 3 are the same as those of Embodiment 1 shown in FIGS. 1 and 2. Blood that is introduced into the housing 32 from an inlet port 8 passes through the hollow fiber membrane 3 on the entrance side and thereafter flows into the first blood channel 7.

With the above-described configuration, when a fluid such as blood is introduced from the inlet port 8, air that is present in the housing 32 of the heat exchanger 1B and air (air bubbles) mixed in the introduced fluid first come into contact with the hollow fiber membrane 3 and are discharged therethrough to the outside. Therefore, for example, during priming, which is performed by introducing a priming liquid such as a physiological saline solution, air can be removed from the interior of the heat exchanger 1B beforehand by the hollow fiber membrane 3. As a result, the priming operation can be simplified and expedited. Moreover, the heat exchanger 1B is effective also in the case where air is mixed in blood during blood circulation after priming is finished, and the mixed air can be eliminated.

Figure 8:
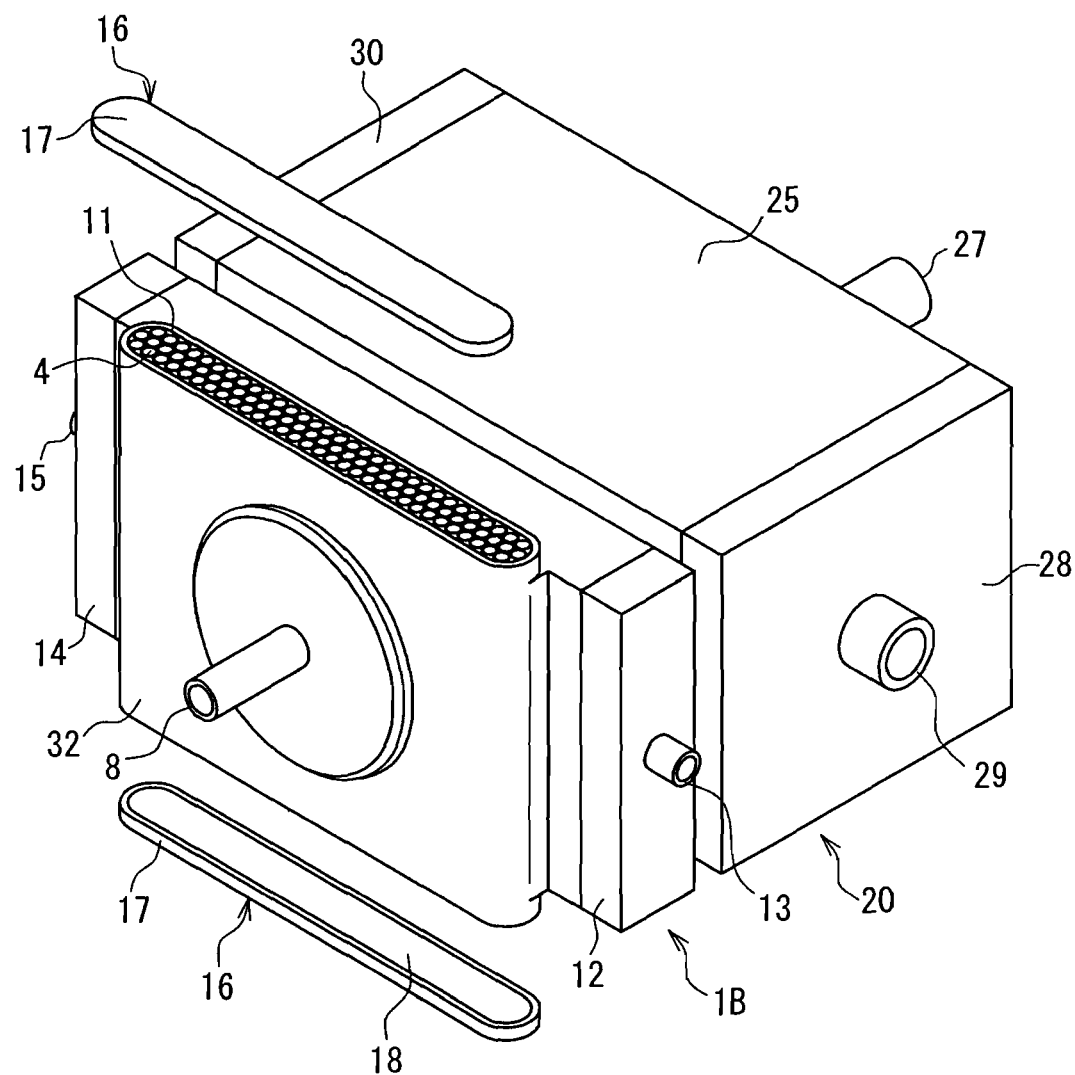
FIG. 8 is a perspective view showing an external appearance of the artificial heart-lung machine in which the same heat exchanger is provided with cap members.

In the present embodiment, the hollow fiber membrane 3 can have the same configuration as that of Embodiment 1. Moreover, it is preferable to take the same measures to address blood plasma leakage as those of Embodiment 1 shown in FIGS. 3 to 5. That is to say, it is preferable that the heat exchanger 1B is provided with cap members 16 shown in FIG. 8. FIG. 8 is a perspective view showing an external appearance of the artificial heart-lung machine provided with the cap members according to the present embodiment. In FIG. 8, the same elements as those of the heat exchanger 1A shown in FIG. 3 are given the same reference numerals to simplify the description thereof.

The heat exchanger 1B with the cap members 16 attached thereto is the same as the heat exchanger 1A with the cap members attached thereto shown in FIG. 4 and, therefore, will be described with reference to also FIG. 4. As shown in FIGS. 8 and 4, the cap members 16 are attached to the openings 11 provided in the housing 32 of the heat exchanger 1B so as to cover those openings. In the present embodiment, the cap members 16 are attached after priming is finished.

The cap members 16 also may be in the form shown in FIG. 5. In the example shown in FIG. 5, the cap members each include the tube 19 instead of the sheet member 18 (see FIG. 4). The use of the cap members 16 shown in FIG. 5 enables the user to seal and unseal the openings 11 with a simple operation.

Embodiment 3

Figure 9:
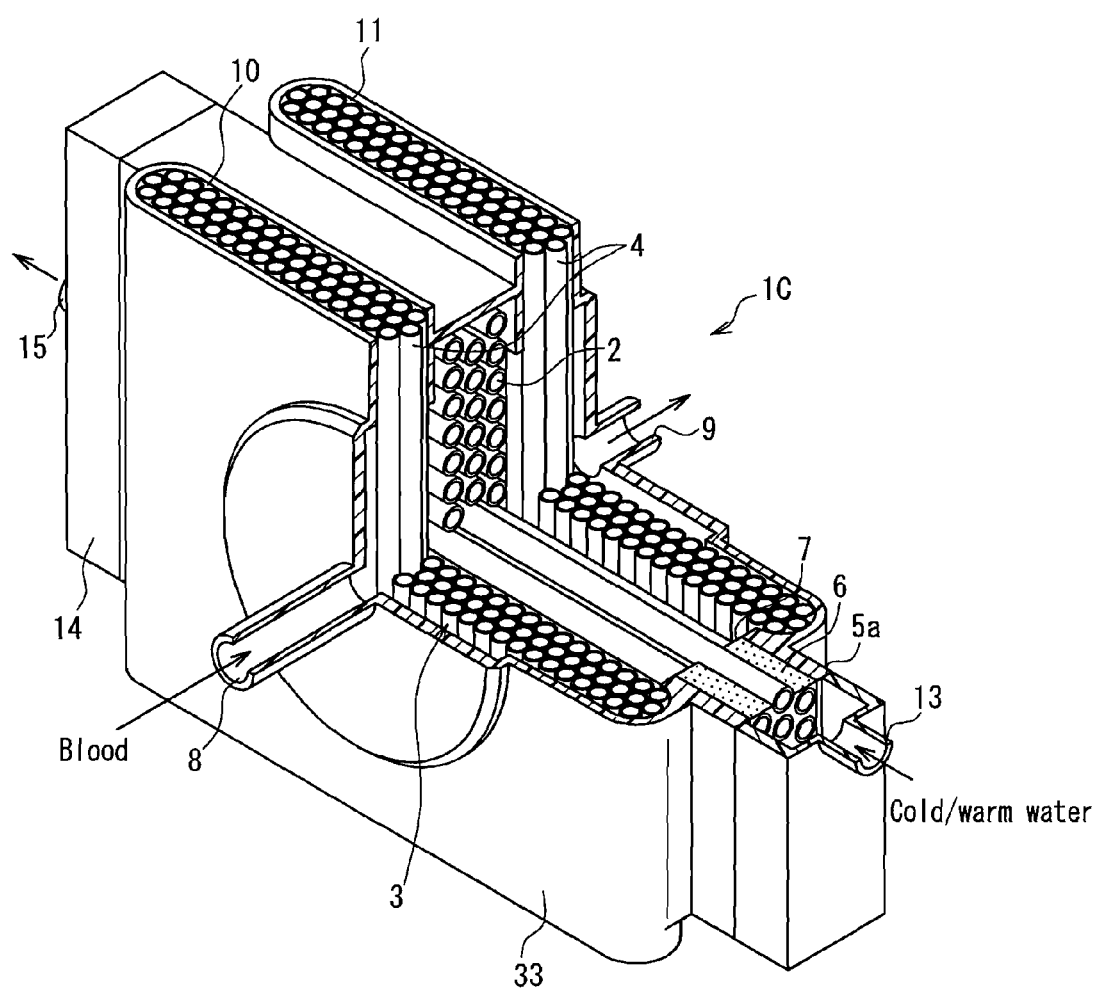
FIG. 9 is a perspective view schematically showing a configuration of a heat exchanger for medical use according to Embodiment 3 of the present invention.
Figure 10:
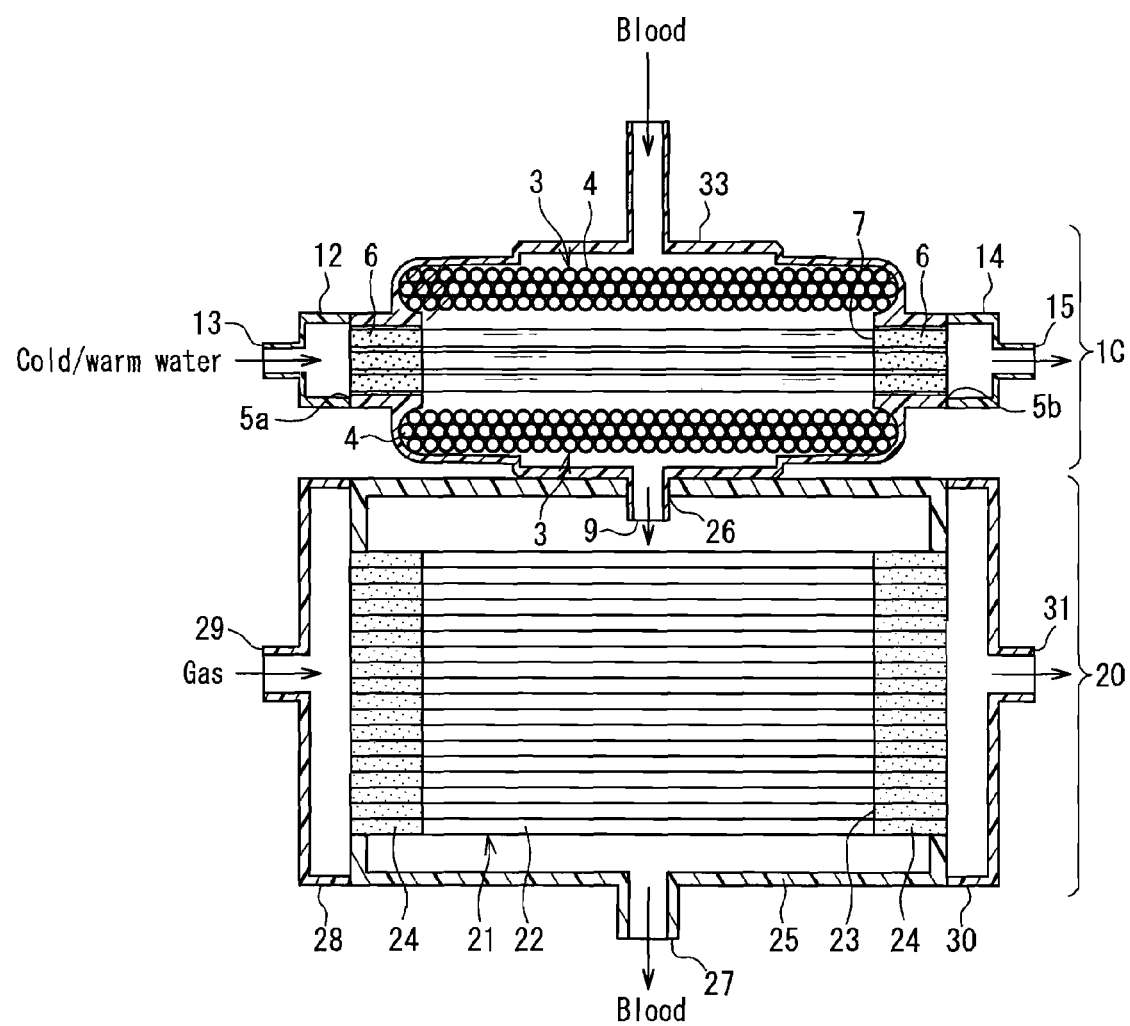
FIG. 10 is a cross-sectional view schematically showing a configuration of an artificial heart-lung machine including the same heat exchanger for medical use.

The configurations of a heat exchanger and an artificial heart-lung machine according to Embodiment 3 of the present invention will be described using FIGS. 9 and 10. FIG. 9 is a perspective view schematically showing the configuration of a heat exchanger 1C of the present embodiment. FIG. 10 is a cross-sectional view schematically showing the configuration of an artificial heart-lung machine including the heat exchanger 1C of the present embodiment. It should be noted that in FIGS. 9 and 10, the same elements as those of the heat exchanger 1A or 1B and the artificial heart-lung machine of Embodiment 1 shown in FIGS. 1 and 2 or Embodiment 2 shown in FIGS. 6 and 7 are given the same reference numerals to simplify the description thereof.

As shown in FIGS. 9 and 10, in the heat exchanger 1C of the present embodiment, hollow fiber membranes 3 are disposed on both of an entrance side and an exit side of a first blood channel 7 in a housing 33. Moreover, the housing 33 includes openings 10 and openings 11 to expose open ends of each of hollow fibers 4 disposed on the entrance side and the exit side to the outside.

In the present embodiment, blood that is introduced into the housing 33 from an inlet port 8 passes through the hollow fiber membrane 3 on the entrance side and flows into the first blood channel 7, and then passes through the hollow fiber membrane 3 on the exit side before flowing into a gas-exchanging portion 20 (see FIG. 10) from a outlet port 9.

In this manner, in the present embodiment, air is removed on both of the entrance side and the exit side of the first blood channel 7 in the heat exchanger 1C. The present embodiment is effective particularly in, during priming, removing air that collects within the heat exchanger 1C. Moreover, after priming, air bubbles mixed in the fluid can be removed more reliably.

As shown in FIGS. 9 and 10, in the present embedment, the hollow fiber membrane 3 on the entrance side and the hollow fiber membrane 3 on the exit side are the same hollow fiber membranes; however, this is not a limitation. In the present embodiment, the material for forming the hollow fibers, the number of hollow fiber sheets, or the like may be different between the hollow fiber membranes 3 on the entrance side and the exit side.

Moreover, also in Embodiment 3, it is preferable that the heat exchanger 1C and the artificial heart-lung machine are provided with cap members as in the cases of Embodiments 1 and 2. Cap members used in the present embodiment will be described using FIGS. 11 to 13.

Figure 11:
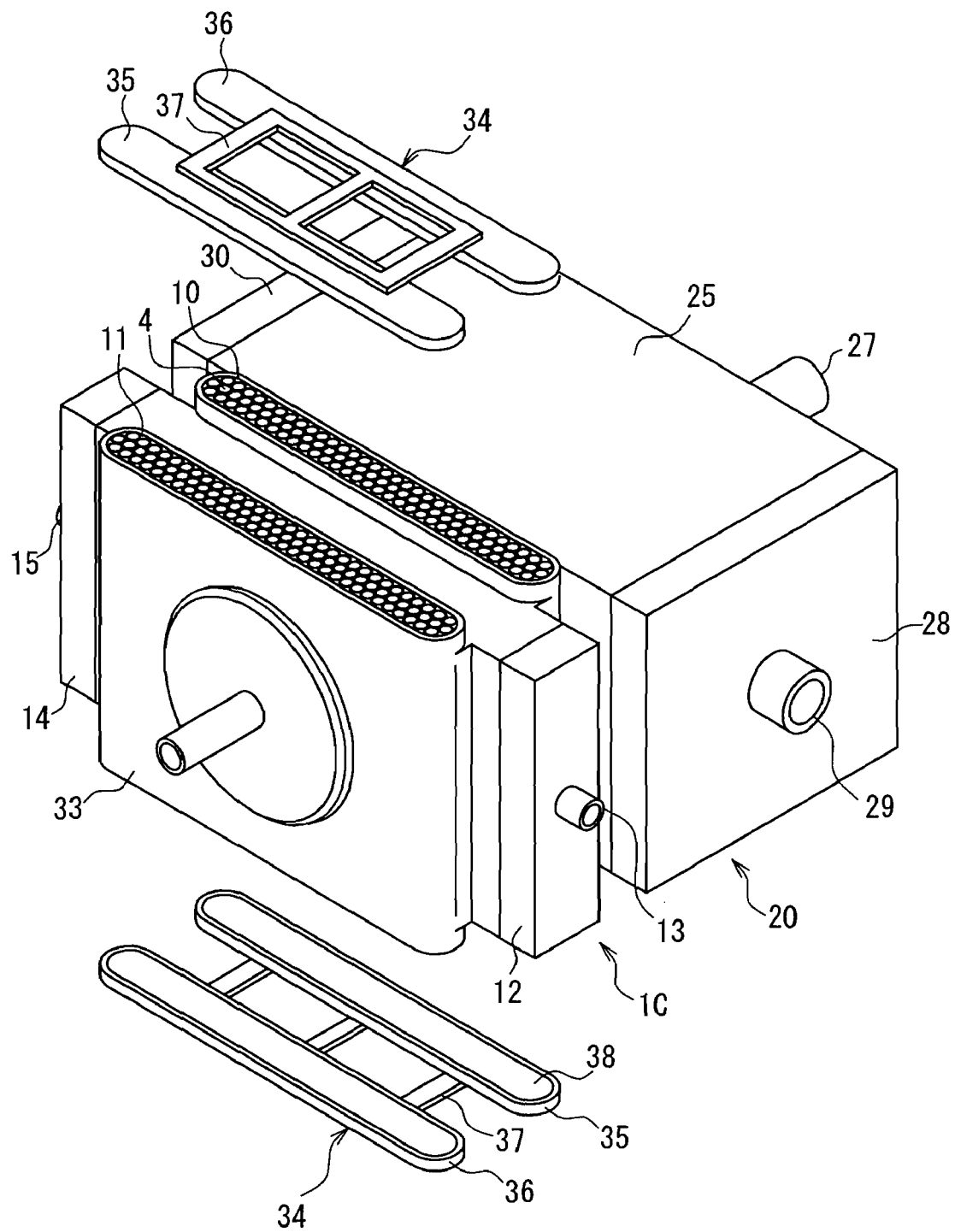
FIG. 11 is a perspective view showing an external appearance of the artificial heart-lung machine in which the same heat exchanger for medical use is provided with cap members.
Figure 12:
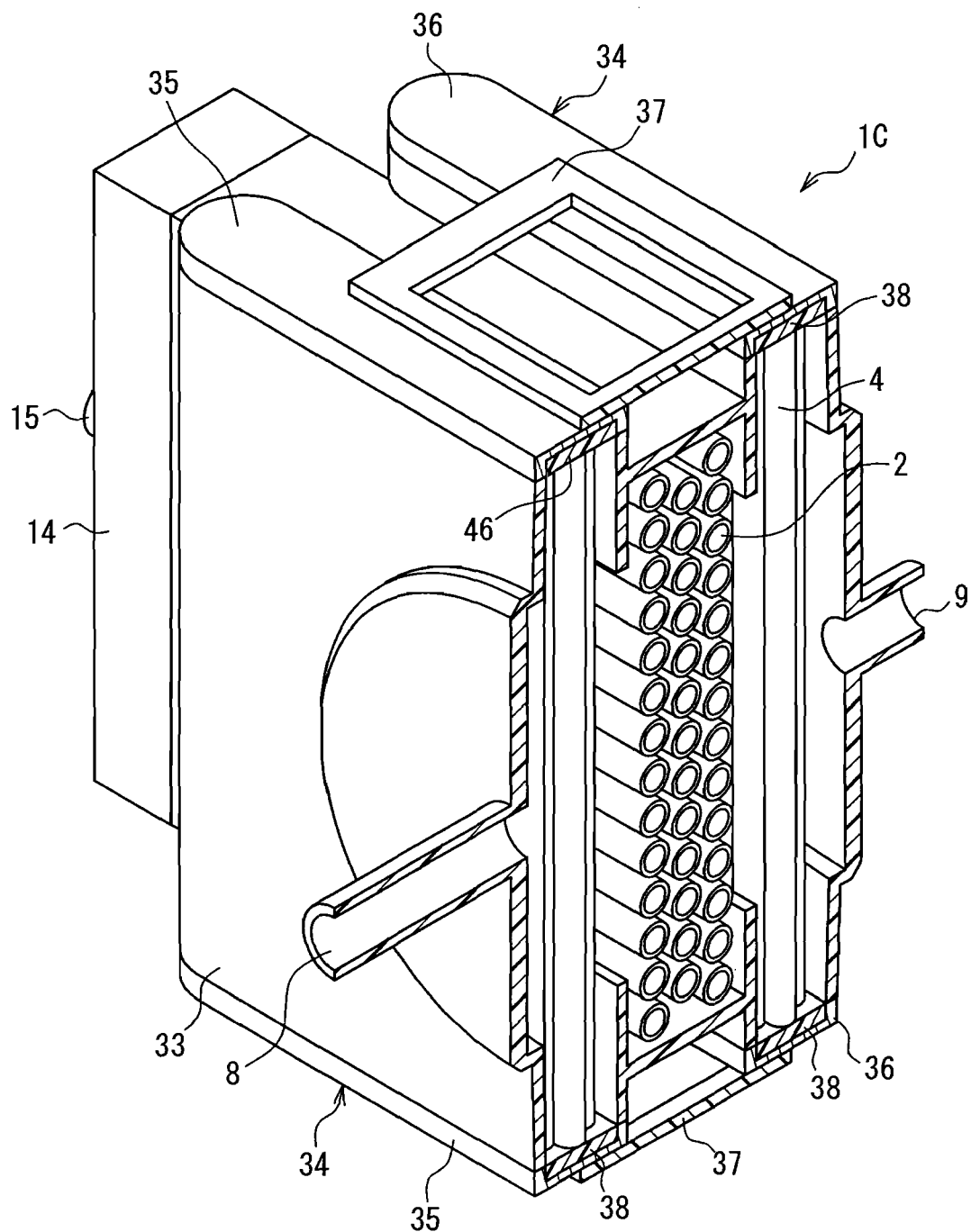
FIG. 12 is a cutaway perspective view showing the same heat exchanger with the cap members attached thereto.
Figure 13:
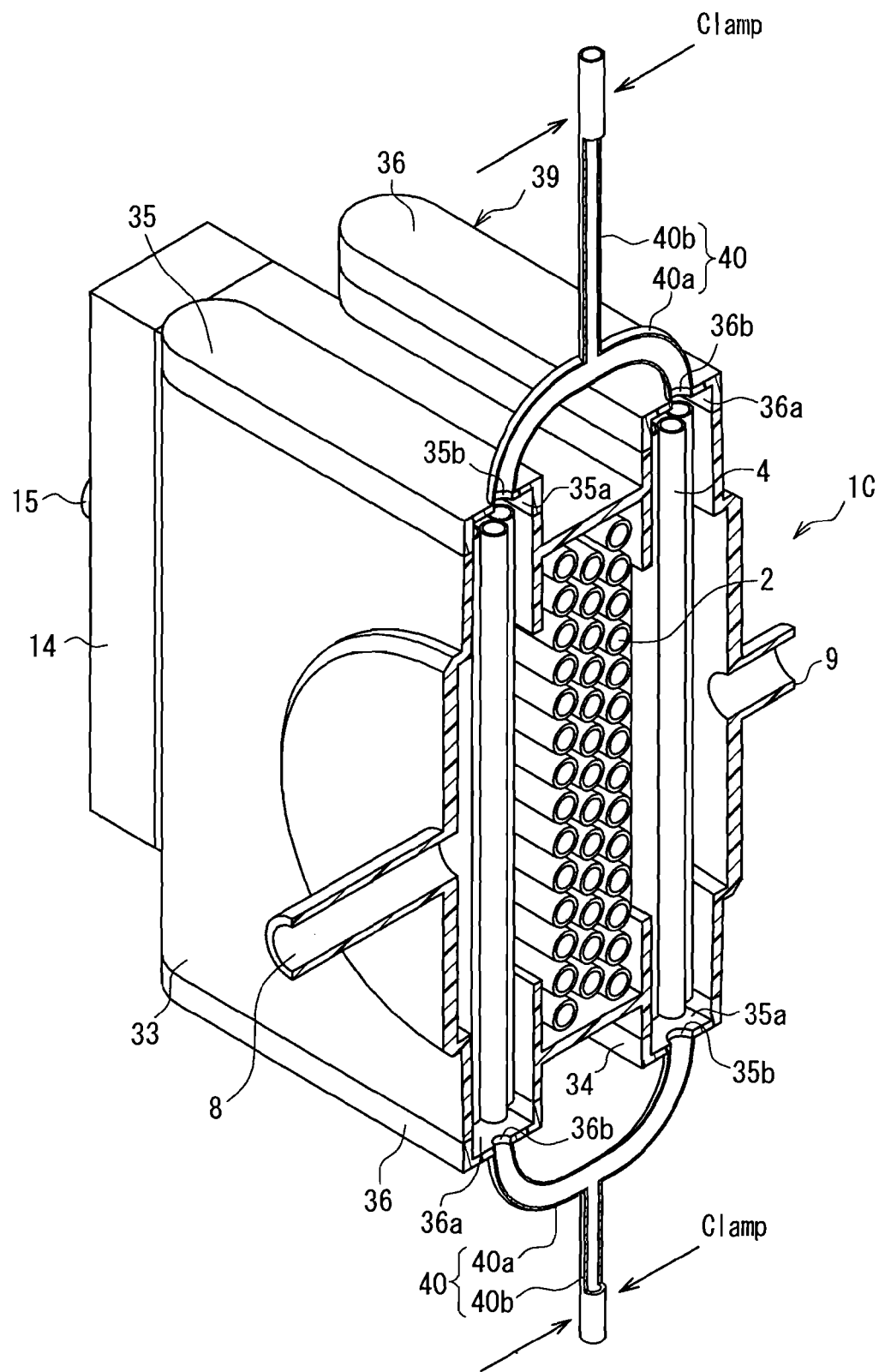
FIG. 13 is a cutaway perspective view showing the same heat exchanger with cap members of another form attached thereto.

FIG. 11 is a perspective view showing an external appearance of the artificial heart-lung machine provided with cap members 34 according to the present embodiment. FIG. 12 is a cutaway perspective view showing the heat exchanger with the cap members 34 attached thereto. FIG. 13 is a cutaway perspective view of the heat exchanger with cap members 39 of another form attached thereto.

The cap members 34 shown in FIGS. 11 and 12 are each formed by preparing two cap members 16 shown in FIGS. 3 and 4 and coupling them together. Specifically, the cap members 34 each include caps 35 and 36 to be attached respectively to the openings 10 and 11. The cap 35 and the cap 36 are coupled together by a bridge member 37. Moreover, a sheet member 38 is disposed inside each of the caps 35 and 36.

Therefore, as shown in FIG. 12, when the sheet members 38 are attached so as to be aligned with the openings 10 and 11 of the housing 33, the hollow fibers of the two hollow fiber membranes 3 are no longer in an open state. Accordingly, also in the present embodiment, even when the hollow fibers 4 of the two hollow fiber membranes 3 come into contact with blood over a prolonged period of time and lose their hydrophobicity, blood cannot intrude into the interior of the hollow fibers 4 through the pores on the side walls thereof thus, blood plasma leakage is suppressed.

Moreover, in the present embodiment, the cap members 39 in a form shown in FIG. 13 also can be used. The cap members 39 shown in FIG. 13 do not include the sheet members 38 like the cap members 16 shown in FIG. 5 and instead include tubes 40. The tubes 40 each include a coupling tube 40a that connects a space 35a on the inside of the cap 35 and a space 36a on the inside of the cap 36 to each other and a ventilating tube 40b branched off from the coupling tube 40a. An open end of the ventilating tube 40b is in an open state.

Therefore, even in the form shown in FIG. 13, after the ventilating tubes 40b are obstructed by clamping the ventilating tubes 40b, the openings 10 and 11 are in a sealed state, and the hollow fibers 4 are no longer in an open state, as in the case of the form shown in FIG. 5. Also in this case, it becomes difficult for a fluid to enter and exit the hollow fibers 4, and blood plasma leakage is suppressed. The use of the cap members 39 shown in FIG. 13 enables the user to seal and unseal the openings 10 and 11 with a simple operation as is the case with the cap members 16 shown in FIG. 5.

INDUSTRIAL APPLICABILITY

According to the heat exchanger for medical use of the present invention, an air-removal function can be provided without any reduction in the heat exchange efficiency, and the heat exchanger is useful as a heat exchanger for use in an artificial heart-lung machine.

The invention claimed is:

1. A heat exchanger for medical use comprising:
   a plurality of tubes through an inner cavity of which a heat-transfer medium liquid flows;
   a sealing member that seals the plurality of tubes while exposing both ends thereof, with a blood channel passing outside each of the tubes being formed in a central portion in an axial direction of the tubes; and
   a housing that accommodates the tubes sealed with the sealing member,
   wherein the heat exchanger further comprises a hollow fiber membrane that is formed of a plurality of hydrophobic and gas permeable hollow fibers and that is disposed on at least one of an entrance side and an exit side of the blood channel in the housing so that a liquid flowing through the blood channel passes through the hollow fiber membrane; and
   the housing comprises openings for exposing open ends of each of the hollow fibers forming the hollow fiber membrane to an area outside the housing, and gaps between an inner side of the openings and the hollow fibers are sealed.

2. The heat exchanger for medical use according to claim 1, further comprising cap members that are attached to the openings of the housing and that seal the openings.

3. The heat exchanger for medical use according to claim 1, wherein the hollow fiber membrane is formed by stacking a plurality of hollow fiber sheets formed by bundling a plurality of hollow fibers into a sheet form.

4. The heat exchanger for medical use according to claim 3, wherein the hollow fiber is made of a porous polypropylene; and
   the hollow fiber membrane is formed by stacking three to five hollow fiber sheets.

5. An artificial heart-lung machine comprising:
   a heat-exchanging portion having a first blood channel and a gas-exchanging portion having a second blood channel, the heat-exchanging portion being arranged so that heat exchange is performed on blood flowing through the first blood channel, the gas-exchanging portion being arranged so that gas exchange is performed on blood flowing through the second blood channel, and the first blood channel and the second blood channel being in communication with each other, allowing a liquid to flow through the two blood channels;

the heat-exchanging portion comprising a plurality of tubes through an inner cavity of which a heat-transfer medium liquid flows, a first sealing member that seals the plurality of tubes while exposing both ends thereof, with a blood channel passing outside each of the tubes being formed in a central portion in an axial direction of the tubes, and a housing that accommodates the tubes sealed with the first sealing member; and the gas-exchanging portion comprising a first hollow fiber membrane formed of a plurality of hydrophobic and gas permeable hollow fibers, and a second sealing member that seals the first hollow fiber membrane while exposing both ends of the hollow fibers, with the second blood channel being formed so as to traverse the plurality of hollow fibers while coming into contact with an outer surface thereof, wherein the heat-exchanging portion further comprises a second hollow fiber membrane that is formed of a plurality of hydrophobic and gas permeable hollow fibers and that is disposed on at least one of an entrance side and an exit side of the first blood channel in the housing so that a liquid flowing through the first blood channel passes through the second hollow fiber membrane; and the housing comprises openings for exposing open ends of each of the hollow fibers forming the second hollow fiber membrane to an area outside the housing, and gaps between an inner side of the openings and the hollow fibers are sealed.

6. The artificial heart-lung machine according to claim 5, further comprising cap members that are attached to the openings of the housing in the heat-exchanging portion and that seal the openings.

7. The artificial heart-lung machine according to claim 5, wherein the hollow fiber membrane is formed by stacking a plurality of hollow fiber sheets formed by bundling a plurality of hollow fibers into a sheet form.

8. The artificial heart-lung machine according to claim 7, wherein the hollow fibers are made of a porous polypropylene, and the hollow fiber membrane is formed by stacking three to five hollow fiber sheets.

* * * * *